US012672815B2

(12) United States Patent
Javault

(10) Patent No.:    US 12,672,815 B2
(45) Date of Patent:        Jul. 7, 2026

(54) QUANTIFICATION OF A PROBABILITY OF A STROKE CONDITION OCCURRENCE VIA MACHINE LEARNING BASED ON FACIAL, BODY MOVEMENTS AND WORD PRONUNCIATION

(71) Applicant: AI STROKE, Perols (FR)

(72) Inventor: Cedric Javault, Perols (FR)

( * ) Notice:    Subject to any disclaimer, the term of this patent is extended or adjusted under 35 U.S.C. 154(b) by 0 days.

(21) Appl. No.: 18/991,836

(22) Filed:    Dec. 23, 2024

(65)                Prior Publication Data

US 2026/0174377 A1      Jun. 25, 2026

(51) Int. Cl.
A61B 5/00          (2006.01)
A61B 5/11          (2006.01)

(52) U.S. Cl.
CPC .......... A61B 5/4064 (2013.01); A61B 5/0077 (2013.01); A61B 5/1128 (2013.01); A61B 5/4803 (2013.01); A61B 5/7267 (2013.01); A61B 5/7275 (2013.01); A61B 2576/02 (2013.01)

(58) Field of Classification Search
CPC ... A61B 5/4064; A61B 5/0077; A61B 5/1128; A61B 5/4803; A61B 5/7267; A61B 5/7275; A61B 2576/02
See application file for complete search history.

(56)                References Cited

U.S. PATENT DOCUMENTS

2025/0079003 A1*    3/2025    Yilmaz .................. G06N 3/092

* cited by examiner

*Primary Examiner* — Serkan Akar
(74) *Attorney, Agent, or Firm* — Patshegen IP; Moshe Pinchas

(57)                ABSTRACT

The method of quantification of an occurrence probability of a stroke condition, comprises the steps of:
    providing, by a computer interface, instructions to a user,
    capturing a series of images and sounds of the user during the execution of each instruction,
    extracting, by a computing device, features from each series captured,
    providing the extracted features for each instruction to a dedicated trained machine learning model, said trained machine learning model being trained to associate an intermediate quantified value of an occurrence probability of a stroke condition,
    receiving the several intermediate quantified value of an occurrence probability of a stroke condition,
    providing the several received intermediate quantified value of an occurrence probability of a stroke condition to a trained machine learning model, said trained machine learning model being trained to associate a final quantified value of an occurrence probability of a stroke condition with several intermediate quantified values of an occurrence probability of a stroke,
    receiving the final quantified value of an occurrence probability of a stroke condition, and
    providing the final quantified value of an occurrence probability of a stroke condition.

8 Claims, 4 Drawing Sheets

300

QUANTIFICATION OF A PROBABILITY OF A STROKE CONDITION OCCURRENCE VIA MACHINE LEARNING BASED ON FACIAL, BODY MOVEMENTS AND WORD PRONUNCIATION

TECHNICAL FIELD OF THE INVENTION

The present invention relates to a method and devices of quantification of an occurrence probability of a stroke condition.

The present invention is applicable to the field of detection and prediction of strokes in human patients.

More generally, the present invention is applicable to the field of medicine.

BACKGROUND OF THE INVENTION

Limiting the effects of strokes on human health require timely medical attention, consisting of two main stages which are diagnosis and treatment of the stroke.

One of the main difficulties is that strokes are often misdiagnosed, leading to the loss of precious time for limiting the effects of said stroke. This misdiagnosis results from the fact that stroke symptoms are varied, inconsistent and complex to detect.

There thus exists a technical need for faster and more accurate stroke detection.

Current systems exist such as disclosed in Parra-Dominguez G S, Sanchez-Yanez R E, Garcia-Capulin C H., Facial Paralysis Detection on Images Using Key Point Analysis. Appl Sci. January 2021; 11 (5): 2435. In such systems, facial paralysis is detected by an artificial intelligence.

Current systems exist such as disclosed in Tongan Cai, Haomiao Ni, Mingli Yu, Xiaolei Huang, Kelvin Wong, John Volpi, James Z. Wang, Stephen T. C. Wong, DeepStroke: An efficient stroke screening framework for emergency rooms with multimodal adversarial deep learning, Medical Image Analysis, Volume 80, 2022, 102522, ISSN 1361-8415. In such systems, an artificial intelligence system is trained to detect a stroke based on two separate videos of a user, along with sound capture of said user.

Current systems exist such as disclosed in Aysen Degerli and Pekka Jakala and Juha Pajula and Milla Immonen and Miguel Bordallo Lopez, MAMAF-Net: Motion-Aware and Multi-Attention Fusion Network for Stroke Diagnosis. In such systems, an artificial intelligence system is trained to detect a stroke based on the execution of four different instructions by a user.

Current systems exist such as disclosed in U.S. Pat. No. 11,699,529. In such systems, an artificial intelligence system is trained to detect a stroke based on image, sound, movement and tactile data collected from a user.

None of these systems provide optimal detection of stroke conditions in a user.

SUMMARY OF THE INVENTION

The present invention is intended to remedy all or part of these disadvantages.

To this effect, according to a first aspect, the present invention aims at a method of quantification of an occurrence probability of a stroke condition, which comprises the steps of:

providing, by a computer interface, at least three instructions to a user, at least three said instructions corresponding to:
- an execution, by the user, of at least one facial movement,
- an execution, by the user, of at least one upper-body movement,
- a pronunciation, by the user, of at least one group of words, capturing, by at least one capturing device, a series of images and sounds of the user during the execution of each instruction, extracting, by a computing device, features from each series captured, providing the extracted features for each instruction to a dedicated trained machine learning model, said trained machine learning model being trained to associate an intermediate quantified value of an occurrence probability of a stroke condition with features representative of series of images of the user during the execution of instructions corresponding to:
- an execution, by the user, of at least one facial movement,
- an execution, by the user, of at least one upper-body movement,
- a pronunciation, by the user, of at least one group of words, receiving, by the computing device, the several intermediate quantified values of an occurrence probability of a stroke condition, providing, on a computer interface, the several received intermediate quantified value of an occurrence probability of a stroke condition to a trained machine learning model, said trained machine learning model being trained to associate a final quantified value of an occurrence probability of a stroke condition with several intermediate quantified values of an occurrence probability of a stroke condition obtained from dedicated trained machine learning models, receiving, by the computing device, the final quantified value of an occurrence probability of a stroke condition, and providing, on a computer interface, the final quantified value of an occurrence probability of a stroke condition.

Such provisions allow for more accurate determination of strokes in human patients. Indeed, the combination of features originating from three series of images linked to facial and body movement and oral pronunciation leads to better training and inference performances.

In particular embodiments, the method object of the present invention comprises, prior to the step of providing the extracted features to a trained machine learning model, a step of concatenating, by the computing device, of the extracted features, said merged features being provided to the trained machine learning model.

Such provisions allow for more accurate determination of strokes in human patients.

In particular embodiments, the method object of the present invention comprises a step of capturing, by at least one capturing device, a series of at least one sound of the user during the execution of at least one instruction, the step of extraction being configured to extract features from each said series of at least one sound.

Such provisions allow for more accurate determination of strokes in human patients. Indeed, the capacity to pronounce groups of words by a user is reflective of the occurrence of a stroke by said user.

In particular embodiments, the step of extracting comprises a step of transforming at least one sound captured into a spectrogram, said spectrogram being used as a feature by the trained machine learning model.

Such provisions allow for more accurate determination of strokes in human patients.

In particular embodiments, the step of extracting features comprises a step of determining at least one position of at least one facial landmark of the face of the user, the method object of the present invention further comprising:

a step of stabilizing, by the computing device, of the extracted facial landmark positions during the execution of at least one facial movement by the user or during the execution of the pronunciation, by the user, of at least one group of words, and a step of transforming, by the computing device, of the stabilized features, said transformed features being provided to a trained machine learning model.

Such provisions allow for more accurate determination of strokes in human patients. Indeed, the ability to move the face of a user is reflective of the occurrence of a stroke by said user.

In particular embodiments, the step of extracting comprises a step of determining, by the computing device, at least one position of at least one wrist of the user along at least one axis in a series of several images of the user during the execution, by the user, of at least one upper-body movement, said at least one position being used as a feature by the trained machine learning model.

Such provisions allow for more accurate determination of strokes in human patients. Indeed, the capacity to move the wrists of a user is reflective of the occurrence of a stroke by said user.

In particular embodiments, the step determining is configured to determine two series of positions of each wrist of the user along at least one axis in a series of images of the user during the execution, by the user, of at least one upper-body movement.

Such provisions allow for more accurate determination of strokes in human patients.

In particular embodiments, the method object of the present invention comprises a step of training a machine learning model to associate a quantified value of an occurrence probability of a stroke condition with features representative of series of images of the user during the execution of instructions corresponding to:

an execution, by a user, of at least one facial movement, an execution, by a user, of at least one upper-body movement, a pronunciation, by a user, of at least one group of words.

In particular embodiments, the method object of the present invention comprises a step of constituting a database of series of empirically measured images and sounds of a user during the execution of instructions corresponding to:

an execution, by the user, of at least one facial movement, an execution, by the user, of at least one upper-body movement, a pronunciation, by the user, of at least one group of words.

In particular embodiments, the method object of the present invention comprises a step of associating a stroke condition identifier with at least one series of empirically measured images and sounds of a user during the execution of instructions corresponding to:

an execution, by the user, of at least one facial movement, an execution, by the user, of at least one upper-body movement, a pronunciation, by the user, of at least one group of words.

According to a second aspect, the present invention aims at a computing device of quantification of an occurrence probability of a stroke condition, which comprises:

one or more processors; and memory storing instructions that, when executed by the one or more processors, cause the computing device to:

providing, by a computer interface, at least three instructions to a user, at least three said instructions corresponding to:

an execution, by the user, of at least one facial movement, an execution, by the user, of at least one upper-body movement, a pronunciation, by the user, of at least one group of words, capturing, by at least one capturing device, a series of images and sounds of the user during the execution of each instruction, extracting, by a computing device, features from each series captured, providing the extracted features for each instruction to a dedicated trained machine learning model, said trained machine learning model being trained to associate an intermediate quantified value of an occurrence probability of a stroke condition with features representative of series of images of the user during the execution of instructions corresponding to:

an execution, by the user, of at least one facial movement, an execution, by the user, of at least one upper-body movement, a pronunciation, by the user, of at least one group of words, receiving, by the computing device, the several intermediate quantified values of an occurrence probability of a stroke condition, providing, on a computer interface, the several received intermediate quantified value of an occurrence probability of a stroke condition to a trained machine learning model, said trained machine learning model being trained to associate a final quantified value of an occurrence probability of a stroke condition with several intermediate quantified values of an occurrence probability of a stroke condition obtained from dedicated trained machine learning models, receiving, by the computing device, the final quantified value of an occurrence probability of a stroke condition, and providing, on a computer interface, the final quantified value of an occurrence probability of a stroke condition.

According to a third aspect, the present invention aims at one or more non-transitory computer-readable media storing instructions that, when executed by one or more processors, cause a computing device to:

providing, by a computer interface, at least three instructions to a user, at least three said instructions corresponding to:

an execution, by the user, of at least one facial movement, an execution, by the user, of at least one upper-body movement, a pronunciation, by the user, of at least one group of words, capturing, by at least one capturing device, a series of images and sounds of the user during the execution of each instruction, extracting, by a computing device, features from each series captured, providing the extracted features for each instruction to a dedicated trained machine learning model, said trained machine learning model being trained to associate an intermediate quantified value of an occurrence probability of a stroke condition with features representative of series of images of the user during the execution of instructions corresponding to:

an execution, by the user, of at least one facial movement, an execution, by the user, of at least one upper-body movement, a pronunciation, by the user, of at least one group of words, receiving, by the computing device, the several intermediate quantified values of an occurrence probability of a stroke condition, providing, on a computer interface, the several received intermediate quantified value of an occurrence probability of a stroke condition to a trained machine learning model, said trained machine learning model being trained to associate a final quantified value of an occurrence probability of a stroke condition with several intermediate quantified values of an occurrence probability of a stroke condition obtained from dedicated trained machine learning models, receiving, by the computing device, the final quantified value of an occurrence probability of a stroke condition, and providing, on a computer interface, the final quantified value of an occurrence probability of a stroke condition.

The following presents a simplified summary of various aspects described herein. This summary is not an extensive overview and is not intended to identify key or critical elements or to delineate the scope of the claims. The following summary merely presents some concepts in a simplified form as an introductory prelude to the more detailed description provided below.

Aspects described herein may allow for improvements in the manner in which strokes are detected and predicted using predictive modeling. The improvements described herein relate to using a set of series of images and/or sounds captured in relation to a set of precise instructions to be followed by a user. The ability to have an early detection may provide users and medical professionals with opportunities for intervention before the onset of a stroke in a patient.

BRIEF DESCRIPTION OF THE DRAWINGS

Other advantages, purposes and particular characteristics of the invention shall be apparent from the following non-exhaustive description of at least one particular embodiment of the present invention, in relation to the drawings annexed hereto, in which.

DETAILED DESCRIPTION OF THE INVENTION

Figure 1:
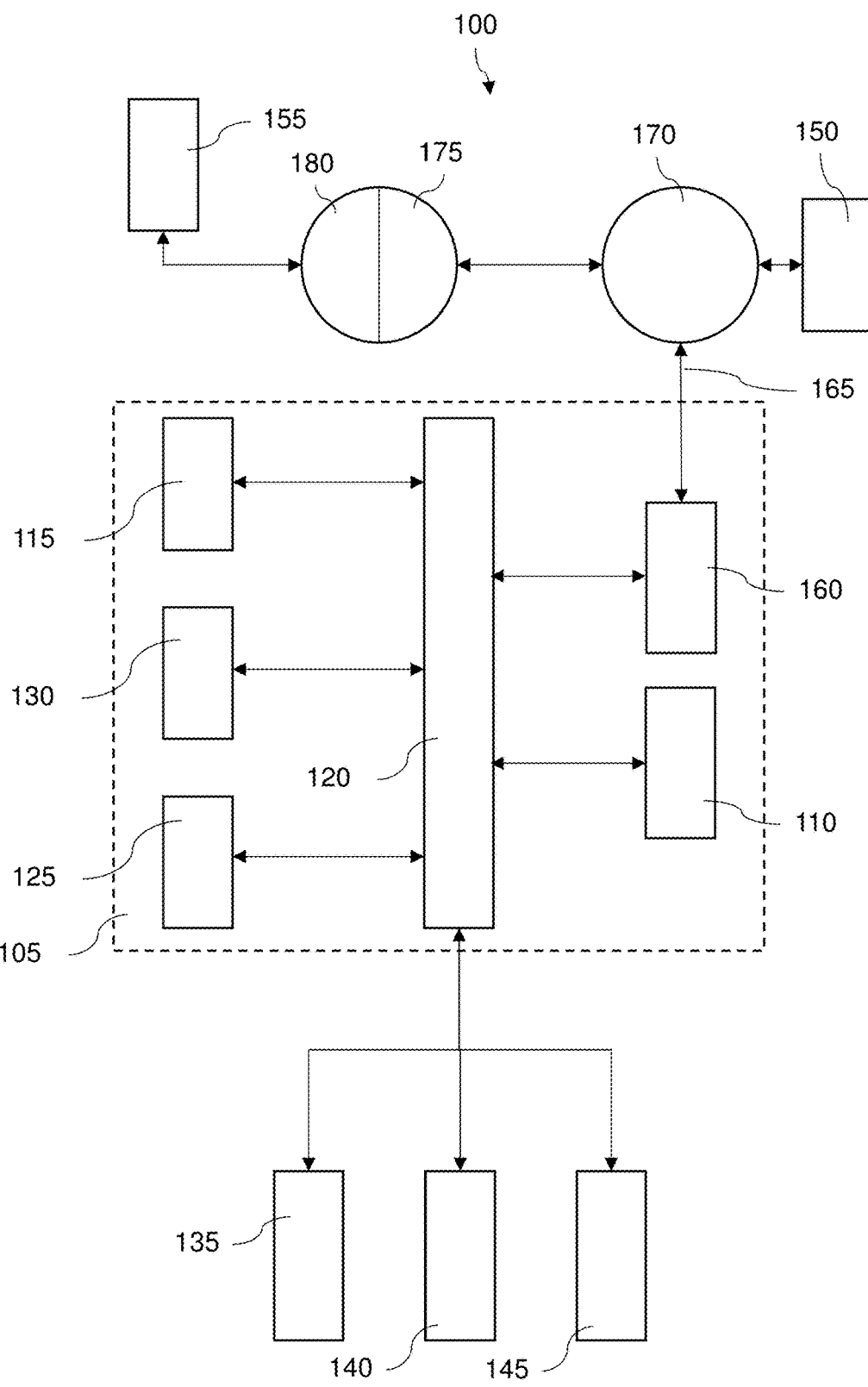
FIG. 1 depicts an example of a computing device that may be used in implementing one or more aspects of the disclosure in accordance with one or more illustrative aspects discussed herein.

This description is not exhaustive, as each feature of one embodiment may be combined with any other feature of any other embodiment in an advantageous manner. Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The indefinite articles 'a' and 'an', as used herein in the specification and in the claims, unless clearly indicated to the contrary, should be understood to mean 'at least one'.

The phrase 'and/or', as used herein in the specification and in the claims, should be understood to mean 'either or both' of the elements so conjoined, i.e., elements that are conjunctively present in some cases and disjunctively present in other cases. Multiple elements listed with 'and/or' should be construed in the same fashion, i.e. 'one or more' of the elements so conjoined. Other elements may optionally be present other than the elements specifically identified by the 'and/or' clause whether related or unrelated to those elements specifically identified. Thus, as a non-limiting example, a reference to 'A and/or B', when used in conjunction with open-ended language such as 'comprising' can refer, in one embodiment, to A only (optionally including elements other than B); in another embodiment, to B only (optionally including elements other than A); in yet another embodiment, to both A and B (optionally including other elements); etc.

As used herein in the specification and in the claims, 'or' should be understood to have the same meaning as 'and/or' as defined above. For example, when separating items in a list, 'or' or 'and/or' shall be interpreted as being inclusive, i.e., the inclusion of at least one, but also including more than one of a number or list of elements, and, optionally, additional unlisted items. Only terms clearly indicated to the contrary, such as 'only one of' or 'exactly one of', or, when used in the claims, 'consisting of', will refer to the inclusion of exactly one element of a number or list of elements. In general, the term 'or' as used herein shall only be interpreted as indicating exclusive alternatives (i.e. 'one or the other but not both') when preceded by terms of exclusivity, such as 'either,' 'one of,' 'only one of', or 'exactly one of'. 'Consisting essentially of,' when used in the claims, shall have its ordinary meaning as used in the field of patent law.

As used herein in the specification and in the claims, the phrase 'at least one', in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase 'at least one' refers, whether related or unrelated to those elements specifically identified. Thus, as a non-limiting example, 'at least one of A and B' (or, equivalently, 'at least one of A or B', or, equivalently 'at least one of A and/or B') can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as 'comprising,' 'including,' 'carrying,' 'having,' 'containing,' 'involving,' 'holding,' 'composed of', and the like are to be understood to be open-ended, i.e., to mean including but not limited to. Only the transitional phrases 'consisting of' and 'consisting essentially of' shall be closed or semi-closed transitional phrases, respectively.

In a general manner, the terms 'digital identifier' or 'digital representation' refer to any bijective digital representation of a physical item, such as a molecule. Such a digital identifier may correspond to, for example, an entry in a database. A digital identifier may refer to a label representative of the name, chemical structure, or internal reference of an ingredient, for example.

As used herein, the terms "means of inputting" refer to, for example, a keyboard, mouse and/or touchscreen adapted to interact with a computing system in such a way to collect user input. In variants, the means of inputting are logical in nature, such as a network port of a computing system configured to receive an input command transmitted electronically. Such input means may be associated with a GUI (Graphic User Interface) shown to a user or an API (Application programming interface). In other variants, the means of inputting may be a sensor configured to measure a specified physical parameter relevant for the intended use case. Examples of means of inputting are disclosed in regard to FIG. 1.

As used herein, the terms "computing system", "computer", or "computer system" designate any electronic calculation device, whether unitary or distributed, capable of receiving numerical inputs and providing numerical outputs by and to any sort of interface, digital and/or analog. Typically, a computing system designates either a computer executing a software having access to data storage or a client-server architecture wherein the data and/or calculation is performed at the server side while the client side acts as an interface. Examples of such computing systems are disclosed in regard to FIG. 1.

FIG. 1 further represents a block diagram that illustrates an example computer system 100 with which an embodiment of the present invention may be implemented. In the example of FIG. 1, a computer system 105 and instructions for implementing the disclosed technologies in hardware, software, or a combination of hardware and software, are represented schematically, for example as boxes and circles, at the same level of detail that is commonly used by persons of ordinary skill in the art to which this disclosure pertains for communicating about computer architecture and computer systems implementations.

The computer system 105 includes an input/output (IO) subsystem 120 which may include a bus and/or other communication mechanism(s) for communicating information and/or instructions between the components of the computer system 105 over electronic signal paths. The I/O subsystem 120 may include an I/O controller, a memory controller and at least one I/O port. The electronic signal paths are represented schematically in the drawings, for example as lines, unidirectional arrows, or bidirectional arrows.

At least one hardware processor 110 is coupled to the I/O subsystem 120 for processing information and instructions. Hardware processor 110 may include, for example, a general-purpose microprocessor or microcontroller and/or a special-purpose microprocessor such as an embedded system or a graphics processing unit (GPU) or a digital signal processor or ARM processor. Processor 110 may comprise an integrated arithmetic logic unit (ALU) or may be coupled to a separate ALU.

Computer system 105 includes one or more units of memory 125, such as a main memory, which is coupled to I/O subsystem 120 for electronically digitally storing data and instructions to be executed by processor 110. Memory 125 may include volatile memory such as various forms of random-access memory (RAM) or other dynamic storage devices. Memory 125 also may be used for storing temporary variables or other intermediate information during execution of instructions to be executed by processor 110. Such instructions, when stored in non-transitory computer-readable storage media accessible to processor 110, can render computer system 105 into a special-purpose machine that is customized to perform the operations specified in the instructions.

Computer system 105 further includes non-volatile memory such as read only memory (ROM) 130 or other static storage device coupled to the I/O subsystem 120 for storing information and instructions for processor 110. The ROM 130 may include various forms of programmable ROM (PROM) such as erasable PROM (EPROM) or electrically erasable PROM (EEPROM). A unit of persistent storage 115 may include various forms of non-volatile RAM (NVRAM), such as FLASH memory, or solid-state storage, magnetic disk, or optical disk such as CD-ROM or DVD-ROM and may be coupled to I/O subsystem 120 for storing information and instructions. Storage 115 is an example of a non-transitory computer-readable medium that may be used to store instructions and data which when executed by the processor 110 cause performing computer-implemented methods to execute the techniques herein.

The instructions in memory 125, ROM 130 or storage 115 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, Internet access applications, design and manufacturing applications, graphics applications, audio applications, software engineering applications, educational applications, games or miscellaneous applications. The instructions may be implemented by a web server, web application server or web client. The instructions may be organized as a presentation layer, application layer and data storage layer such as a relational database system using structured query language (SQL) or no SQL, an object store, a graph database, a flat file system or other data storage.

Computer system 105 may be coupled via I/O subsystem 120 to at least one output device 135. In one embodiment, output device 135 is a digital computer display or Human Machine Interface. Examples of a display that may be used in various embodiments include a touchscreen display or a light-emitting diode (LED) display or a liquid crystal display (LCD) or an e-paper display. Computer system 105 may include other type(s) of output devices 135, alternatively or in addition to a display device. Examples of other output devices 135 include printers, ticket printers, plotters, projectors, sound cards or video cards, speakers, buzzers or piezoelectric devices or other audible devices, lamps or LED or LCD indicators, haptic devices, actuators, or servos.

At least one input device 140 is coupled to I/O subsystem 120 for communicating signals, data, command selections or gestures to processor 110. Examples of input devices 140 include touchscreens, microphones, still and video digital cameras, alphanumeric and other keys, keypads, keyboards, graphics tablets, image scanners, joysticks, clocks, switches, buttons, dials, slides.

Another type of input device is a control device 145, which may perform cursor control or other automated control functions such as navigation in a graphical interface on a display screen, alternatively or in addition to input functions. Control device 145 may be a touchpad, a mouse, a trackball, or cursor direction keys for communicating direction information and command selections to processor 110 and for controlling cursor movement on display 135. The input device may have at least two degrees of freedom in two axes, a first axis (e.g., x) and a second axis (e.g., y), that allows the device to specify positions in a plane. Another type of input device is a wired, wireless, or optical control device such as a joystick, wand, console, steering wheel, pedal, gearshift mechanism or other type of control device. An input device 140 may include a combination of multiple different input devices, such as a video camera and a depth sensor.

In another embodiment, computer system 105 may comprise an Internet of things (IoT) device in which one or more of the output device 135, input device 140, and control device 145 are omitted. Or, in such an embodiment, the input device 140 may comprise one or more cameras, motion detectors, thermometers, microphones, seismic detectors, other sensors or detectors, measurement devices or encoders and the output device 135 may comprise a special-purpose display such as a single-line LED or LCD display, one or more indicators, a display panel, a meter, a valve, a solenoid, an actuator or a servo.

Computer system 105 may implement the techniques described herein using customized hard-wired logic, at least one ASIC or FPGA, firmware and/or program instructions or logic which when loaded and used or executed in combination with the computer system causes or programs the computer system to operate as a special-purpose machine. According to one embodiment, the techniques herein are performed by computer system 105 in response to processor 110 executing at least one sequence of at least one instruction contained in main memory 125. Such instructions may be read into main memory 125 from another storage medium, such as storage 115. Execution of the sequences of instructions contained in main memory 125 causes processor 110 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical or magnetic disks, such as storage 115. Volatile media includes dynamic memory, such as memory 125. Common forms of storage media include, for example, a hard disk, solid state drive, flash drive, magnetic data storage medium, any optical or physical data storage medium, memory chip, or the like.

Storage media is distinct from but may be used in conjunction with transmission media. Transmission media participates in transferring information between storage media. For example, transmission media includes coaxial cables, copper wire and fiber optics, including the wires that comprise a bus of I/O subsystem 120. Transmission media can also take the form of acoustic or light waves, such as those generated during radio-wave and infrared data communications.

Various forms of media may be involved in carrying at least one sequence of at least one instruction to processor 110 for execution. For example, the instructions may initially be carried on a magnetic disk or solid-state drive of a remote computer. The remote computer can load the instructions into its dynamic memory and send the instructions over a communication link such as a fiber optic or coaxial cable or telephone line using a modem. A modem or router local to computer system 105 can receive the data on the communication link and convert the data to a format that can be read by computer system 105. For instance, a receiver such as a radio frequency antenna or an infrared detector can receive the data carried in a wireless or optical signal and appropriate circuitry can provide the data to I/O subsystem 120 such as place the data on a bus. I/O subsystem 120 carries the data to memory 125, from which processor 110 retrieves and executes the instructions. The instructions received by memory 125 may optionally be stored on storage 115 either before or after execution by processor 110.

Computer system 105 also includes a communication interface 160 coupled to bus 120. Communication interface 160 provides a two-way data communication coupling to network link(s) 165 that are directly or indirectly connected to at least one communication network, such as a network 170 or a public or private cloud on the Internet. For example, communication interface 160 may be an Ethernet networking interface, integrated-services digital network (ISDN) card, cable modem, satellite modem, or a modem to provide a data communication connection to a corresponding type of communications line, for example an Ethernet cable or a metal cable of any kind or a fiber-optic line or a telephone line. Network 170 broadly represents a local area network (LAN), wide-area network (WAN), campus network, internet, or any combination thereof. Communication interface 160 may comprise a LAN card to provide a data communication connection to a compatible LAN, or a cellular radiotelephone interface that is wired to send or receive cellular data according to cellular radiotelephone wireless networking standards, or a satellite radio interface that is wired to send or receive digital data according to satellite wireless networking standards. In any such implementation, communication interface 160 sends and receives electrical, electromagnetic, or optical signals over signal paths that carry digital data streams representing various types of information.

Network link 165 typically provides electrical, electromagnetic, or optical data communication directly or through at least one network to other data devices, using, for example, satellite, cellular, Wi-Fi, or BLUETOOTH technology. For example, network link 165 may provide a connection through a network 170 to a host computer 150.

Furthermore, network link 165 may provide a connection through network 170 or to other computing devices via internetworking devices and/or computers that are operated by an Internet Service Provider (ISP) 175. ISP 175 provides data communication services through a world-wide packet data communication network represented as Internet 180. A server computer 155 may be coupled to Internet 180. Server 155 broadly represents any computer, data center, virtual machine, or virtual computing instance with or without a hypervisor, or computer executing a containerized program system such as DOCKER or KUBERNETES. Server 155 may represent an electronic digital service that is implemented using more than one computer or instance and that is accessed and used by transmitting web services requests, uniform resource locator (URL) strings with parameters in HTTP payloads, API calls, app services calls, or other service calls. Computer system 105 and server 155 may form elements of a distributed computing system that includes other computers, a processing cluster, server farm or other organization of computers that cooperate to perform tasks or execute applications or services. Server 155 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, Internet access applications, design and manufacturing applications, graphics applications, audio applications, software engineering applications, educational applications, games or miscellaneous applications. Server 155 may comprise a web application server that hosts a presentation layer, application layer and data storage layer such as a relational database system using structured query language (SQL) or no SQL, an object store, a graph database, a flat file system or other data storage.

Computer system 105 can send messages and receive data and instructions, including program code, through the network(s), network link 165 and communication interface 160. In the Internet example, a server 155 might transmit a requested code for an application program through Internet 180, ISP 175, local network 170 and communication interface 160. The received code may be executed by processor 110 as it is received, and/or stored in storage 115, or other non-volatile storage for later execution.

The execution of instructions as described in this section may implement a process in the form of an instance of a computer program that is being executed and consists of program code and its current activity. Depending on the operating system (OS), a process may be made up of multiple threads of execution that execute instructions concurrently. In this context, a computer program is a passive collection of instructions, while a process may be the actual execution of those instructions. Several processes may be associated with the same program; for example, opening up several instances of the same program often means more than one process is being executed. Multitasking may be implemented to allow multiple processes to share processor 110. While each processor 110 or core of the processor executes a single task at a time, computer system 105 may be programmed to implement multitasking to allow each processor to switch between tasks that are being executed without having to wait for each task to finish. In an embodiment, switches may be performed when tasks perform input/output operations, when a task indicates that it can be switched, or on hardware interrupts. Time-sharing may be implemented to allow fast response for interactive user applications by rapidly performing context switches to provide the appearance of concurrent execution of multiple processes simultaneously. In an embodiment, for security and reliability, an operating system may prevent direct communication between independent processes, providing strictly mediated and controlled inter-process communication functionality.

Figure 2:
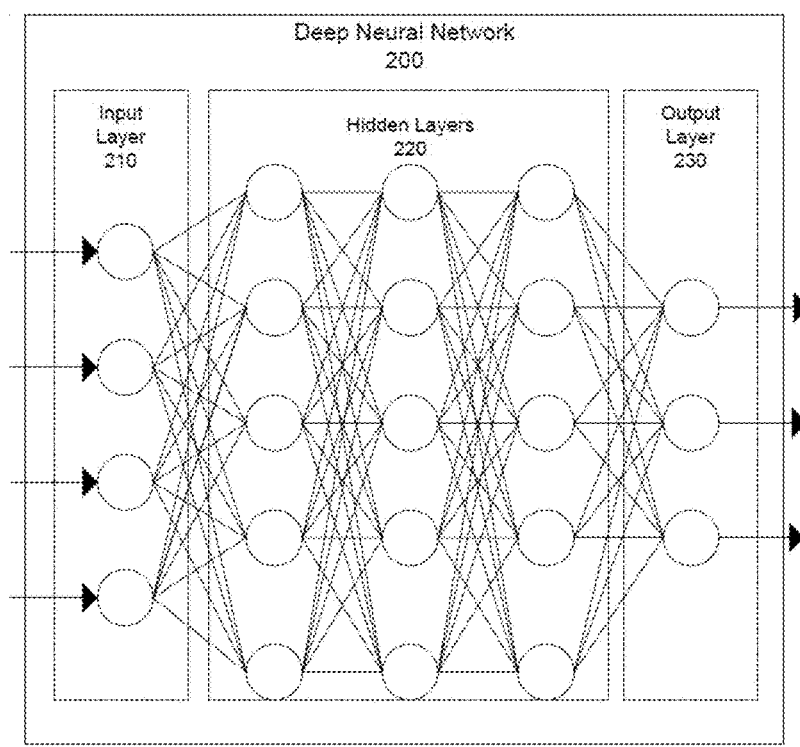
FIG. 2 depicts an example deep neural network architecture for a model according to one or more aspects of the disclosure.

FIG. 2 illustrates an example deep neural network architecture 200. Such a deep neural network architecture might be all or portions of a machine learning model. That said, the architecture depicted in FIG. 2 need not be performed on a single computing device, and might be performed by, e.g., a plurality of computers. A machine learning model may be a collection of connected nodes; with the nodes and connections each having assigned weights used to generate predictions. Each node in the machine learning model may receive input and generate an output signal. The output of a node in the machine learning model may be a function of its inputs, and the weights associated with the edges. Ultimately, the trained model may be provided with input beyond the training set and used to generate predictions regarding the likely results. Machine learning models may have many applications, including object classification, image recognition, speech recognition, natural language processing, text recognition, regression analysis, behavior modeling, and others.

A machine learning model may have an input layer 210, one or more hidden layers 220, and an output layer 230. A deep neural network, as used herein, may be an artificial network that has more than one hidden layer. Illustrated network architecture 200 is depicted with three hidden layers, and thus may be considered a deep neural network. The number of hidden layers employed in deep neural network 200 may vary based on the particular application and/or problem domain. For example, a network model used for image recognition may have a different number of hidden layers than a network used for speech recognition. Similarly, the number of input and/or output nodes may vary based on the application. Many types of deep neural networks are used in practice, such as convolutional neural networks, recurrent neural networks, feed forward neural networks, combinations thereof, and others.

During the model training process, the weights of each connection and/or node may be adjusted in a learning process as the model adapts to generate more accurate predictions on a training set. The weights assigned to each connection and/or node may be referred to as the model parameters. The model may be initialized with a random or white noise set of initial model parameters. The model parameters may then be iteratively adjusted using, for example, stochastic gradient descent algorithms that seek to minimize errors in the model.

Figure 3:
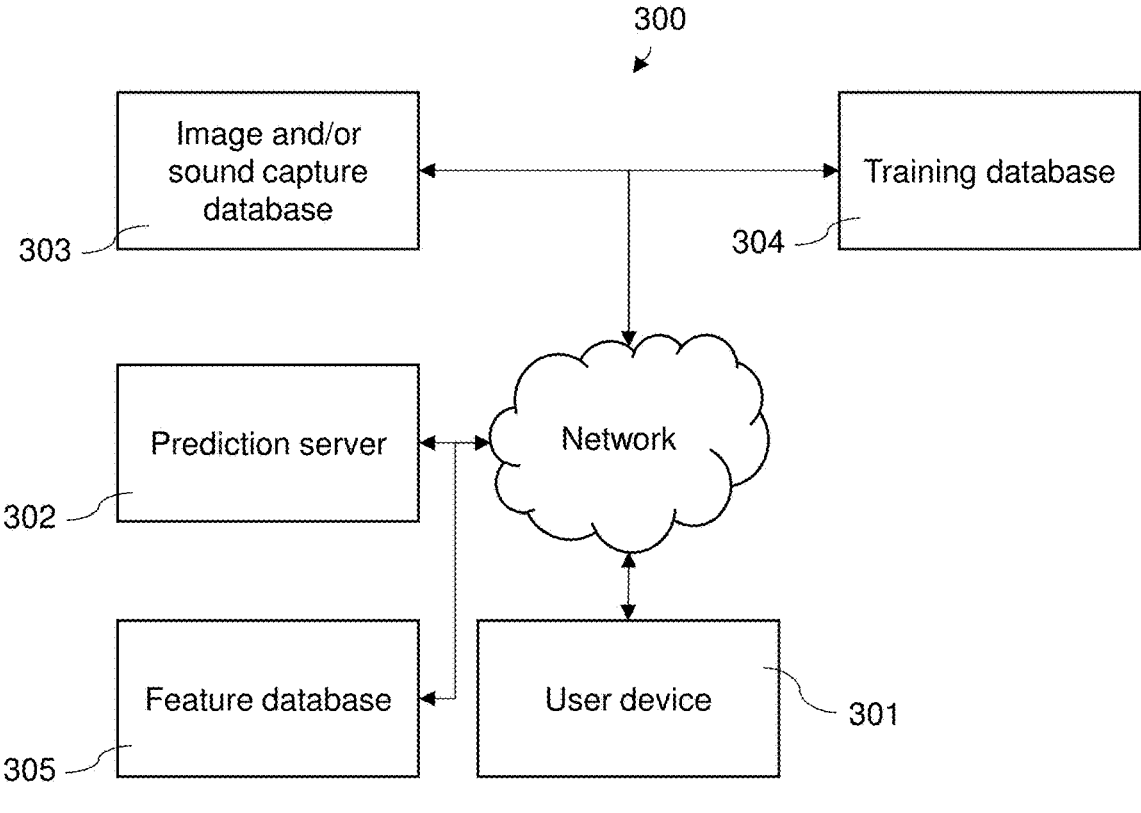
FIG. 3 depicts a system comprising different computing devices that may be used in implementing one or more aspects of the disclosure in accordance with one or more illustrative aspects discussed herein.

FIG. 3 depicts a system for processing image and/or sound data from a user device 301. The user device 301 is shown as connected, via a network, such as shown in FIG. 1, to a prediction server 302, an image and/or sound capture database 303, a training database 304, a feature database 305. The image and/or sound capture database 303, training database 304 and the feature database 305 may reside in a same database or separate database. Each of the user device 301, the prediction server 302, the image and/or sound capture database 303, the training database 304 and/or the feature database 305 may be one or more computing devices, such as a computing device comprising one or more processors and memory storing instructions that, when executed by the one or more processors, perform one or more steps as described further herein. For example, any of those devices might be the same or similar as the computing device of FIG. 1.

As part of the prediction process, the user device 301 might communicate, via the network, to access the prediction server 302 for a request for evaluating a stroke condition of one or more users. As noted, the user device 301 and the prediction server 302 may correspond to the same device. The user device 301 may be a component in a (point of care) system that may also include a point of care device, and/or a drug administering device and/or a stroke treatment device. The user device 301 shown here might be a smartphone, laptop, or the like, and the nature of the communications between the two might be via the Internet or the like. For example, the user device 301 might access a website associated with the prediction server 302, and the user device 301 might provide (e.g., over the Internet and by filling out an online form) candidate authentication credentials to that website. The prediction server 302 may then determine whether the authentication credentials are valid. For example, the prediction server 302 might compare the candidate authentication credentials received from the user device 301 with authentication credentials stored by a user account database (not shown in FIG. 3). The user device may be a device that is suitable for performing point of care testing to assess the symptoms of a stroke.

The image and/or sound capture database 303 might comprise series of images and/or sound associated with specific instructions measured by the user device 301 such as a smartphone device. The image and/or sound data stored by the image and/or sound capture database 303 may include records indicating a record identifier, a name of the image and/or sound file, a description, at least one corresponding extracted feature, an identifier of a user, an age of the user, a measurement date and/or time, or the like. The image and/or sound data stored by the image and/or sound capture database 303 might be generated based on one or more capture conducted by one or more users.

The training database 304 may include pre-labelled stroke condition data and other data related to a training set of patients. Data stored by the training database 304 and the image and/or sound capture database 303 may but need not be related. For example, the records stored by the training database 303 may include additional information, such as the gender of the user, a country of origin of the user, and the like. The prediction system may use the records in the training database 304 to train a machine learning model to determine features that may be indicative to a stroke condition.

The feature database 305 may comprise data indicative of a stroke condition. The feature database 305 may include records indicating features that may be indicative of a stroke condition. The feature database 305 may include features that may be indicative to a stroke condition based on additional factors such as a gender or an age of the users, blood pressure or other vital sign monitoring signal, and the like. The feature database 305 may include features that may be indicative of a stroke condition based on a combination of factors as discussed above. The feature database 305 may store a weight associated with each of the features. The weight factor may indicate how important the corresponding feature contributes to a prediction of a stroke condition for the susceptible users.

The prediction server 302 may use a predictive algorithm (e.g., one or more machine learning models) to determine whether one or more users may be susceptible to a stroke condition. The machine learning model may be trained using training data from the training database 304 including historical image and/or sound data from different users and predefined or predetermined labels indicating whether the users are susceptible to a stroke condition. For example, the training data may comprise data indicating, for each of hundreds of different users, a corresponding stroke condition value. The stroke condition model generates a probability that the user may belong to each class (e.g., positive or negative) based on a stroke condition threshold. The output of the machine learning model might be reported as a probability (e.g., the stroke condition value) or a binary prediction (e.g., positive or negative). The machine learning model might be a supervised model. The historical image and/or sound data in 304 may include information which is similar to the content of the image and/or sound capture database 303. This information together with the corresponding stroke condition values may be used to train the machine learning model.

Figure 4:
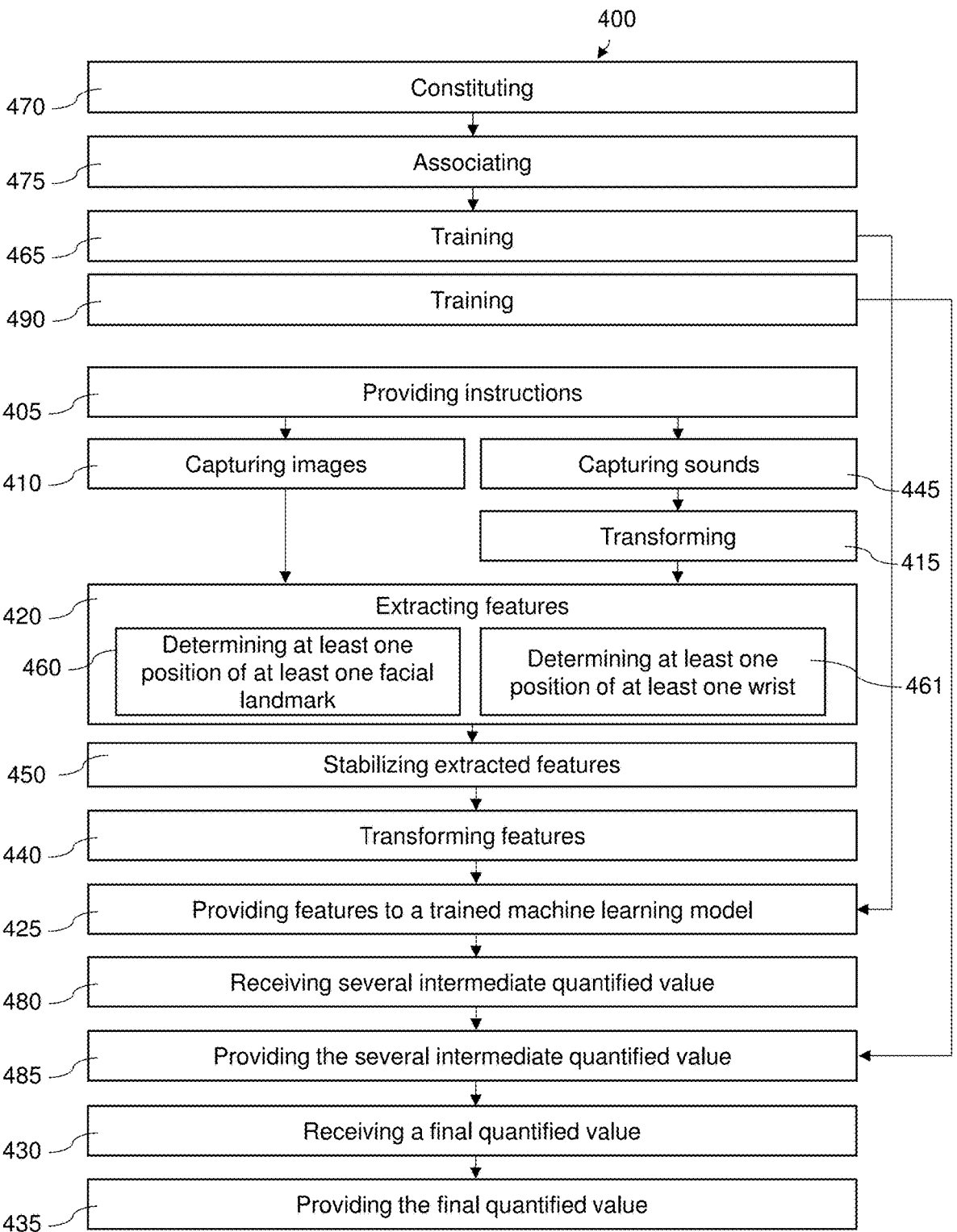
FIG. 4 depicts a flow chart comprising steps which may be performed for the execution of the method object of the present invention.

Multiple different machine learning models may be used at different times to predict whether a user is susceptible to a stroke condition. For example, the prediction server 302 may use a second machine learning model to identify potential features that may be indicative of a stroke condition. The prediction server may use a third machine learning model to determine a customized stroke condition threshold tailored for users susceptible to specific comorbidities. FIG. 4 shows, schematically, a particular succession of steps of the method 400 object of the present invention. This method of quantification of an occurrence probability of a stroke condition, comprises the steps of:

providing 405, by a computer interface, at least three instructions to a user, at least three said instructions corresponding to:

an execution, by the user, of at least one facial movement, an execution, by the user, of at least one upper-body movement, a pronunciation, by the user, of at least one group of words, capturing 410, by at least one capturing device, a series of images or sounds of the user during the execution of each instruction, extracting 420, by a computing device, features from each series captured, providing 425 the extracted features for each instruction to a dedicated trained machine learning model, said trained machine learning model being trained to associate an intermediate quantified value of an occurrence probability of a stroke condition with features representative of series of images or sounds of the user during the execution of instructions corresponding to:

an execution, by the user, of at least one facial movement, an execution, by the user, of at least one upper-body movement, a pronunciation, by the user, of at least one group of words, receiving 480, by the computing device, the several intermediate quantified value of an occurrence probability of a stroke condition, providing 485, on a computer interface, the several received intermediate quantified value of an occurrence probability of a stroke condition to a trained machine learning model, said trained machine learning model being trained to associate a final quantified value of an occurrence probability of a stroke condition with several intermediate quantified values of an occurrence probability of a stroke condition obtained from dedicated trained machine learning models, receiving 430, by the computing device, the final quantified value of an occurrence probability of a stroke condition, and providing 435, on a computer interface, the final quantified value of an occurrence probability of a stroke condition.

The step of providing 405 is performed, for example, by executing instructions, corresponding to a computer software, by a computing system, such as the one shown in FIG. 1.

During this step of providing 405, an output device 135 such as shown in FIG. 1 is used. This output device 135 may correspond to a computer or smartphone screen associated with a graphic user interface or to a logical interface, such as an application programming interface for example.

During this step of providing 405 instructions may be provided to a user in the form of text, video and/or audio messages displayed on a graphic user interface. These instructions are shown in sequence according to a predetermined sequence.

For example, these instructions correspond to:

an execution, by the user, of at least one facial movement, then an execution, by the user, of at least one upper-body movement, then a pronunciation, by the user, of at least one group of words.

At least one facial movement can correspond to a smiling instruction, a puffing of the cheeks instruction, a closing of the eyes as much as possible, a raise of eyebrow instruction, a blowing a candle instruction or a kissing a baby instruction. A patient suffering from a stroke condition may not be able to properly execute these instructions.

In other embodiments, the step of providing 405 is configured to provide a succession of instructions corresponding to at least one, two, three, four, five or six facial movements.

At least one upper-body movement can correspond to raising at least one arm, and preferably both arms, for a determined amount of time (such as ten seconds, for example). A patient suffering from a stroke condition might not be able to properly execute these instructions. In particular, in the case where both arms are to be raised, both arms will not raise at the same time or in the same manner.

At least one pronunciation of at least one group of words can correspond to reading a few sentences in a list of predetermined sentences or a randomized list of words. It can also for example correspond to repeating a few words. A patient suffering from a stroke condition might not be able to properly execute these instructions. In respect to this instruction, two symptoms are sought: aphasia, where patients will not be able to read the words and dysarthria where patients will not be able to pronounce the words.

The step of capturing 410 a series of images and/or sounds of the user during the execution of each instruction is performed for example, by a video camera or webcam associated to a computing device allowing the storing or processing of said at least one image.

This step of capturing 410 is preferably performed in such a fashion that the key features of the body of the user are apparent and closely framed. For instructions relative to facial movement or pronunciation, the framing is preferably close to and facing the face whereas for instructions relative to upper-body, the framing is preferably close to the upper-body. In particular embodiments, if a movement of the face of the user to one side is detected, the instructions are restarted.

During this step of capturing, a graphic user interface may indicate to the user if the proximity between the image capturing device is suitable. Such an evaluation can be the result of an image processing algorithm configured to detect a body feature (an arm or the face of the user) and determine a size ratio of the body feature in the captured image. If this ratio is above a threshold representative of a suitable size of the body feature, an indication that the distance of the capturing device is suitable may be shown on a graphic user interface of the device. If this ratio is under a threshold representative of a suitable size of the body feature, an indication that the distance of the capturing device is suitable may be shown on a graphic user interface of the device. Likewise, if any one of said thresholds is exceeded in manner that corresponds to an unwanted position of the device, an indication that the distance of the capturing device is unsuitable may be shown on a graphic user interface of the device.

In particular embodiments, the method 400 object of the present invention comprises a step of capturing 445, by at least one capturing device, a series of at least one sound of the user during the execution of at least one instruction, the step 420 of extraction being configured to extract features from each said series of at least one sound.

The step of capturing 445 is performed, for example, by a sound capturing device, such as a microphone. This microphone can be associated with the image capturing device used to capture images of the user performing the instructions provided.

The step of extracting 420 features from each series captured is performed, for example, by executing instructions, corresponding to a computer software, by a computing system, such as the one shown in FIG. 1.

During this step 420 of extracting, predetermined features are extracted from the signal which corresponds to the series of captured images, and/or sounds. The nature of these features may differ based on the corresponding set of instructions associated with the image capture.

In particular embodiments, the method 100 object of the present invention comprises a step of transforming at least one sound captured into a spectrogram, said spectrogram being used as a feature by the trained machine learning model.

In particular embodiments, the method 100 object of the present invention comprises a step of denoising at least one sound captured.

In particular embodiments, the method 100 object of the present invention comprises a step of cutting at least one sound captured to remove sounds which do not originate from the patient.

Such a step of cutting at least one sound is performed by the execution of a speaker identification algorithm, which is well-known in the field of sound signal processing. Once the initial speaker is identified, series of sounds which do not include said identified initial speaker are removed from the series of sounds.

In particular embodiments, a feature extracted corresponds to facial landmark positions in at least one image of the face of the user. Such facial landmarks correspond to predetermined points of all human faces (such as the tip of the nose or the position of the eyes for example). To obtain such positions, a facial landmark recognition algorithm may be used. Such an algorithm may correspond to the Dlib algorithm for example.

In particular embodiments, the step of extracting 420 features comprises a step of determining 460 at least one position of at least one facial landmark of the face of the user, the method object of the present invention further comprising:

a step of stabilizing 450, by the computing device, of the extracted facial landmark positions during the execution of at least one facial movement by the user or during the execution of the pronunciation, by the user, of at least one group of words, and a step of transforming 440, by the computing device, of the stabilized features, said transformed features being provided to a trained machine learning model.

The step of stabilizing 450 features from each series captured is performed, for example, by executing instructions, corresponding to a computer software, by a computing system, such as the one shown in FIG. 1.

Such a step of stabilizing 450 may be performed by the execution of an algorithm that locks landmarks in place in the coordinates of an image stream. For example, the landmark extractors like the Dlib algorithm work separately on each image of a video and can be made more robust and less noisy with this stabilization process that leverage the consecutive nature of the different images in the video. The same might apply for a wrist position extractor.

In particular embodiments, once the features are extracted, a step of transforming 440 the extracted features is performed. Such a step of transforming 440 may be based on stabilized features such as the facial landmark positions predicted, or wrists position extracted.

Such features correspond to, for example, ratios between the positions of predetermined landmark.

Figure 5:
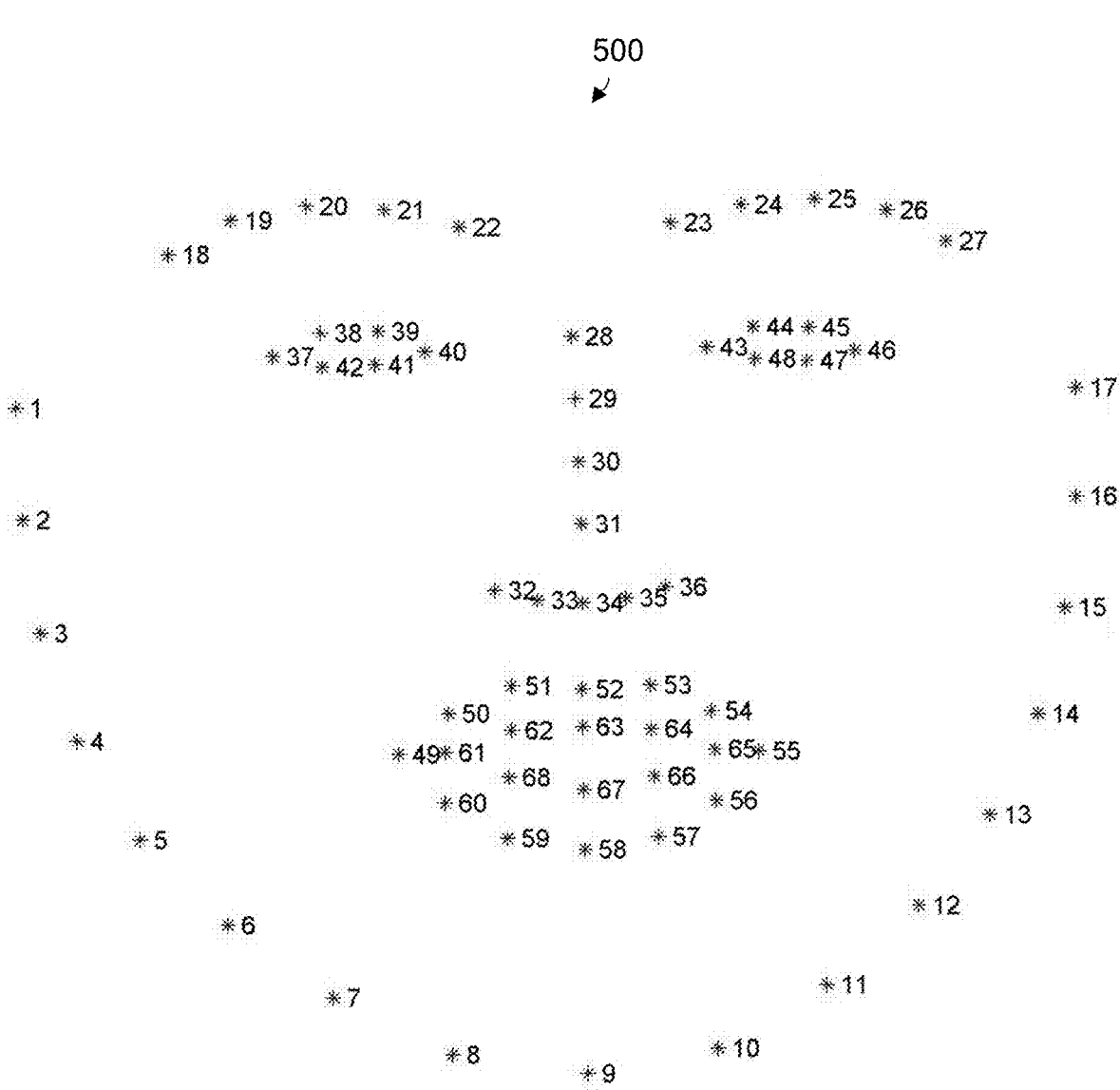
FIG. 5 represents, schematically, facial landmarks that can be identified during execution of a method object of the present invention.

For example, in the case of the face of a user, potential landmarks are identified in FIG. 5, said features corresponding to, for example:

New Feature1 corresponds to the slope of point 39 relative to point 41 where the slope is defined as Delta (x)/Delta (y), New Feature2 corresponds to the slope of point 9 relative to point 28, New Feature3 corresponds to the angle between point the averaged position of points 19, 20, 21, 24, 25 and 26 and point 9, which corresponds to the value in radius of the angle between the vertical and the line passing through both points, New Feature4 corresponds to the maximum between the ratios AE/AF and AF/AE, where AE corresponds to the distance between point 21 and point 41 and AF corresponds to the distance between point 24 and point 48, New Feature5 corresponds to the maximum of the ratios BA/A and BB/A where BA corresponds to the distance between point 9 and point 19, BB corresponds to the distance between point 9 and point 26 and A corresponds to the distance between point 17 and point 1.

In particular embodiments, the method object of the present invention comprises a step of training, or retraining, a facial landmark position prediction algorithm (sur as the Dlib algorithm) for nonsymmetrical faces (typical of patients suffering from a stroke).

It should be noted that prior to the step of extracting features, the method object of the present invention may further comprise a step of selection configured to remove non relevant images from the series of images.

Such a step of selection may for example be configured to remove images of the face of a user in resting position.

In particular embodiments, the method 100 object of the present invention comprises the step of transforming 415 at least one sound captured in a spectrogram, said spectrogram being used as a feature by the trained machine learning model.

The step of transforming 415 at least one sound captured in a spectrogram is performed, for example, by executing instructions, corresponding to a computer software, by a computing system, such as the one shown in FIG. 1.

Such a transformation is well-known in the field of signal processing.

In particular embodiments, the step of extracting 420 comprises a step of determining 461, by the computing device, at least one position of at least one hand of the user along at least one axis in a series of images of the user during the execution, by the user, of at least one upper-body movement, said at least one position being used as a feature by the trained machine learning model.

The step of determining 461 at least one position is performed, for example, by executing instructions, corresponding to a computer software, by a computing system, such as the one shown in FIG. 1.

During the step of determining 461, an image processing algorithm may be performed which is configured to recognize, in an image or in a stream of image, a wrist of a user and, upon recognition, provide the two-dimensional coordinates of said wrist in the captured image.

This method of processing and analyzing motion data begins with the stabilization of the raw video using algorithms such as VidStab. This stabilization step aims to eliminate undesired camera movements, ensuring that only the motion of the filmed subject is retained for further analysis.

Following stabilization, the system performs skeleton extraction. For this purpose, open-source algorithms such as OpenPose or MMPose may be employed to extract the skeletal structure of the subject in the video. Specifically, the algorithm identifies and tracks key points corresponding to the subject's anatomical joints. In this implementation, only the coordinates of the left and right wrist key points are retained for subsequent processing.

Optionally, an additional stabilization step 450 may be introduced to reduce the noise in the extracted key point coordinates. This is achieved by averaging the positions of the key points over a sliding window of 2n+1 frames, between −n to +n, where n represents the number of frames on either side of the current frame. This step ensures smoother temporal data by mitigating the effects of transient variations or inaccuracies in the key point detection process. An additional stabilization using optical flow might be used as well.

The processed coordinates yield four distinct time series: xleft, yleft, xright, and yright, representing the horizontal and vertical positions of the left and right wrists, respectively. Custom heuristics are then applied to determine the start and end points of the activity within the video. These heuristics may rely on changes in motion patterns, position thresholds, or other pre-defined criteria.

To address potential discrepancies caused by variations in video resolution, the coordinate values are normalized to a range between 0 and 1. This normalization process maps the bottom-right corner of the frame to (0,0) and the top-left corner to (1,1), ensuring consistency across different input video resolutions.

Finally, the normalized time series data is input into a deep learning model trained to analyze motion patterns and provide predictions or classifications based on the extracted features. This model leverages the temporal information from the wrist trajectories to perform tasks such as exercise evaluation, motion analysis, or other domain-specific applications.

For example, for the movements of the face of a user, 40 features may be obtained and input into the deep learning model.

For example, for the movements of the wrists of the user, temporal series wherein the y-axis coordinates for the wrists can be obtained and input into the deep learning model.

In particular embodiments, the step determining 461 is configured to determine two series of positions of each wrist of the user along at least one axis in a series of images of the user during the execution, by the user, of at least one upper-body movement.

The step of providing 425 the extracted features to a trained machine learning model is performed, for example, by executing instructions, corresponding to a computer software, by a computing system, such as the one shown in FIG. 1.

During the step of providing 425, the extracted features are transferred to a trained machine learning model, which is operated by a computing device. Such a trained machine learning model may be operated on a smartphone or on a remote server linked, via a communication link, to a computing device associated with the image capture device.

In particular embodiments, series of images corresponding to the following instructions may be captured:

at least one, two, three, four, five or six series of images relative to instructions representative of the movement of the face of the user corresponding to predetermined mimics, such as blowing a candle, smiling, raising eyebrows and so son, at least one series of images relative to instructions representative of the movement of the arms of the user corresponding to raising one's arms, at least one, two, three, four, or five series of images relative to instructions representative of the reading of words or sentences by the user, at least one to at least twenty series of images relative to instructions representative of the repetition of words by the user.

Such embodiments allow for the generation of as many predictions as the number of series captured (or isolated by further video-processing algorithms). Such predictions correspond to intermediate predictions, which can then be fed into a subsequent trained machine learning model to produce a final prediction based on the individual intermediate predictions. The output of the step of providing 425 is at least one classification inference, such as "stroke condition" and "no stroke condition", associated with an inference probability. This output can be stored in a database, provided to an application programming interface or to another software element.

The step of receiving 480 the intermediate quantified value of an occurrence probability of a stroke condition is performed, for example, by executing instructions, corresponding to a computer software, by a computing system, such as the one shown in FIG. 1.

The step of providing 485 the intermediate predictions to a trained machine learning model is performed, for example, by executing instructions, corresponding to a computer software, by a computing system, such as the one shown in FIG. 1.

During the step of providing 485, the intermediate predictions are transferred to a trained machine learning model, which is operated by a computing device. Such a trained machine learning model may be operated on a smartphone or on a remote server linked, via a communication link, to a computing device associated with the image capture device.

The output of the step of providing 485 is at least one classification inference, such as "stroke condition" and "no stroke condition", associated with an inference probability. This output can be stored in a database, displayed upon a user interface, provided to an application programming interface or to another software element.

The step of receiving 430 the quantified value of an occurrence probability of a stroke condition is performed, for example, by executing instructions, corresponding to a computer software, by a computing system, such as the one shown in FIG. 1.

During the step of receiving 430, a computing device, such as the computing device used for the step of capturing 410, receives the quantified value of an occurrence probability of a stroke condition.

The step of providing 435 the quantified value of an occurrence probability of a stroke condition is performed, for example, by executing instructions, corresponding to a computer software, by a computing system, such as the one shown in FIG. 1.

During the step of providing 435, a computer display may be used to show the quantified value of an occurrence probability of a stroke condition to a user. Alternatively, an indicator representative of the quantified value may be provided.

In particular embodiments, the method 100 object of the present invention comprises:

a step of training 465 a plurality of dedicated machine learning model to associate an intermediate quantified value of an occurrence probability of a stroke condition with features representative of series of images of the user during the execution of instructions corresponding to:

an execution, by a user, of at least one facial movement, an execution, by a user, of at least one upper-body movement, a pronunciation, by a user, of at least one group of words, and a step of training 490 a machine learning model being trained to associate a final quantified value of an occurrence probability of a stroke condition with several intermediate quantified values of an occurrence probability of a stroke condition obtained from dedicated trained machine learning models The step of training 465 is performed, for example, by executing instructions, corresponding to a computer software, by a computing system, such as the one shown in FIG. 1.

An example of such a step of training 465 is disclosed in regards of FIG. 3. During such a step, exemplar series of images and/or sounds captured during the execution, by a group of users, of instructions provided to said users are fed to a machine learning model in supervised manner.

During this step of training 465, several distinct and or types of machine learning models may be trained, each dedicated for a specific prediction based on a type of instruction performed by patients and present in the captured images and/or sounds.

For example, a first machine learning model may be trained to infer a stroke condition based on the facial movement of a user when said user is instructed to mimic blowing a candle and a second machine learning model may be trained to infer a stroke condition based on the facial movement of a user when said user is instructed to raise an eyebrow.

For example, a multilayer perceptron (MLP) may be used for the inference of a stroke condition based on series of images representative of the facial movement of a user.

Such a MLP may have, as input, 40 features, two hidden layers with, for example, 128 and 16 neurons, and one output layer.

For example, a support machine classifier may be used for the inference of a stroke condition based on series of images representative of the upper-body movement of a user.

For example, a ResNet18 architecture may be used for the inference of a stroke condition based on series of sounds transformed into spectrogram originating from the user.

Such exemplar series of images and/or sounds may be taken from a database.

The step of training 490 is performed, for example, by executing instructions, corresponding to a computer software, by a computing system, such as the one shown in FIG. 1.

During this step of training 490, intermediate predictions produced by the machine learning models trained during the step of training 465 are used as input to a machine learning model configured to produce an inference or prediction based on available labeled data associated with said predictions.

During this step of training 490, a MLP may be used as base architecture, said MLP comprising as many input as the number of predictions made by the intermediate machine learning models, two hidden layers with 128 then 16 layers for example and one output layer.

In particular embodiments, the method 100 object of the present invention comprises a step of constituting 470 a database of series of empirically measured images and sound of a user during the execution of instructions corresponding to:

an execution, by the user, of at least one facial movement,
an execution, by the user, of at least one upper-body movement,
a pronunciation, by the user, of at least one group of words.

Such a database may be constituted by uploading empirically measured images of a user. Such a database may also store additional information relative to the context of capture or to the user.

In particular embodiments, the method 100 object of the present invention comprises a step of associating 475 a stroke condition identifier with at least one series of empirically measured images of a user during the execution of instructions corresponding to:

an execution, by the user, of at least one facial movement,
an execution, by the user, of at least one upper-body movement,
a pronunciation, by the user, of at least one group of words.

The step of associating 475 is performed, for example, by a user using an input device such as shown in FIG. 1. During this step of associating 475 (or annotating), a user may associate a tag or a value ('0' or '1') associated with a set of series of images and/or sounds, said tag or value being representative of the occurrence of a stroke condition for a user associated with the captured images and/or sounds.

As it is understood, the present invention also aims at a computing device of quantification of an occurrence probability of a stroke condition, which comprises:

one or more processors; and
memory storing instructions that, when executed by the one or more processors, cause the computing device to:
providing, by a computer interface, at least three instructions to a user, at least three said instructions corresponding to:
an execution, by the user, of at least one facial movement,
an execution, by the user, of at least one upper-body movement,
a pronunciation, by the user, of at least one group of words,
capturing, by at least one capturing device, a series of images and sounds of the user during the execution of each instruction,
extracting, by a computing device, features from each series captured,
providing the extracted features for each instruction to a dedicated trained machine learning model, said trained machine learning model being trained to associate an intermediate quantified value of an occurrence probability of a stroke condition with features representative of series of images and sounds of the user during the execution of instructions corresponding to:
an execution, by the user, of at least one facial movement,
an execution, by the user, of at least one upper-body movement,
a pronunciation, by the user, of at least one group of words,
receiving, by the computing device, the several intermediate quantified values of an occurrence probability of a stroke condition,
providing, on a computer interface, the several received intermediate quantified value of an occurrence probability of a stroke condition to a trained machine learning model, said trained machine learning model being trained to associate a final quantified value of an occurrence probability of a stroke condition with several intermediate quantified values of an occurrence probability of a stroke condition obtained from dedicated trained machine learning models, receiving, by the computing device, the final quantified value of an occurrence probability of a stroke condition, and providing, on a computer interface, the final quantified value of an occurrence probability of a stroke condition.

As it is understood, the present invention also aims at one or more non-transitory computer-readable media storing instructions that, when executed by one or more processors, cause a computing device to:

providing, by a computer interface, at least three instructions to a user, at least three said instructions corresponding to:

an execution, by the user, of at least one facial movement, an execution, by the user, of at least one upper-body movement, a pronunciation, by the user, of at least one group of words, capturing, by at least one capturing device, a series of images and sounds of the user during the execution of each instruction, extracting, by a computing device, features from each series captured, providing the extracted features for each instruction to a dedicated trained machine learning model, said trained machine learning model being trained to associate an intermediate quantified value of an occurrence probability of a stroke condition with features representative of series of images and sounds of the user during the execution of instructions corresponding to:

an execution, by the user, of at least one facial movement, an execution, by the user, of at least one upper-body movement, a pronunciation, by the user, of at least one group of words, receiving, by the computing device, the several intermediate quantified values of an occurrence probability of a stroke condition, providing, on a computer interface, the several received intermediate quantified value of an occurrence probability of a stroke condition to a trained machine learning model, said trained machine learning model being trained to associate a final quantified value of an occurrence probability of a stroke condition with several intermediate quantified values of an occurrence probability of a stroke condition obtained from dedicated trained machine learning models, receiving, by the computing device, the final quantified value of an occurrence probability of a stroke condition, and providing, on a computer interface, the final quantified value of an occurrence probability of a stroke condition.

The invention claimed is:

1. Method of quantification of an occurrence probability of a stroke condition, which comprises the steps of:

providing, by a computer interface, at least three instructions to a user, at least three said instructions corresponding to:

an execution, by the user, of at least one facial movement, an execution, by the user, of at least one upper-body movement, a pronunciation, by the user, of at least one group of words, capturing, by at least one capturing device, a series of images and sounds of the user during the execution of each instruction, extracting, by a computing device, features from each series captured, in which the step of extracting comprises a step of determining, by the computing device, at least one position of at least one wrist of the user along at least one axis in a series of images of the user during the execution, by the user, of at least one upper-body movement, said at least one position being used as a feature by the trained machine learning model, in which the step determining is configured to determine two series of positions of each wrist of the user along at least one axis in a series of images of the user during the execution, by the user, of at least one upper-body movement, providing a first trained machine learning model, said first trained machine learning model being trained to associate an intermediate quantified value of an occurrence probability of a stroke condition with features representative of series of images and sounds of the user during the execution of instructions corresponding to:

an execution, by the user, of at least one facial movement, an execution, by the user, of at least one upper-body movement, a pronunciation, by the user, of at least one group of words, providing the extracted features for each instruction to said first trained machine learning model and receiving, by the computing device, the several intermediate quantified values of an occurrence probability of a stroke condition, providing a second trained machine learning model, said second trained machine learning model being trained to classify said several intermediate quantified values using a database containing at least pre-labeled stroke condition data and other data related to a training set of patients;

providing, on a computer interface, the several received intermediate quantified value of an occurrence probability of a stroke condition to said second trained machine learning model and determining a final quantified value of an occurrence probability of a stroke condition in accordance with said several intermediate quantified values receiving, by the computing device, the final quantified value of an occurrence probability of a stroke condition, and providing, on a computer interface, the final quantified value of an occurrence probability of a stroke condition.

2. Method according to claim 1, in which the step of extracting comprises a step of transforming at least one sound captured in a spectrogram, said spectrogram being used as a feature by the trained machine learning model.

3. Method according to claim 1, in which the step of extracting features comprises a step of determining at least one position of at least one facial landmark of the face of the user, the method object of the present invention further comprising:

a step of stabilizing, by the computing device, of the extracted facial landmark positions during the execution of at least one facial movement by the user or during the execution of the pronunciation, by the user, of at least one group of words, and a step of transforming, by the computing device, of the stabilized features, said transformed features being provided to a trained machine learning model.

4. Method according to claim 1, which comprises:

a step of training a plurality of dedicated machine learning model to associate an intermediate quantified value of an occurrence probability of a stroke condition with features representative of series of images and sounds of the user during the execution of instructions corresponding to:

an execution, by a user, of at least one facial movement, an execution, by a user, of at least one upper-body movement, a pronunciation, by a user, of at least one group of words, and a step of training a machine learning model being trained to associate a final quantified value of an occurrence probability of a stroke condition with several intermediate quantified values of an occurrence probability of a stroke condition obtained from dedicated trained machine learning models.

5. Method according to claim 1, which comprises a step of constituting a database of series of empirically measured images and sounds of a user during the execution of instructions corresponding to:

an execution, by the user, of at least one facial movement, an execution, by the user, of at least one upper-body movement, a pronunciation, by the user, of at least one group of words.

6. Method according to claim 1, which comprises a step of associating a stroke condition identifier with at least one series of empirically measured images and sounds of a user during the execution of instructions corresponding to:

an execution, by the user, of at least one facial movement, an execution, by the user, of at least one upper-body movement, a pronunciation, by the user, of at least one group of words.

7. Computing device of quantification of an occurrence probability of a stroke condition, which comprises:

one or more processors; and memory storing instructions that, when executed by the one or more processors, cause the computing device to:

providing, by a computer interface, at least three instructions to a user, at least three said instructions corresponding to:

an execution, by the user, of at least one facial movement, an execution, by the user, of at least one upper-body movement, a pronunciation, by the user, of at least one group of words, capturing, by at least one capturing device, a series of images and sounds of the user during the execution of each instruction, extracting, by a computing device, features from each series captured, in which the step of extracting comprises a step of determining, by the computing device, at least one position of at least one wrist of the user along at least one axis in a series of images of the user during the execution, by the user, of at least one upper-body movement, said at least one position being used as a feature by the trained machine learning model, in which the step determining is configured to determine two series of positions of each wrist of the user along at least one axis in a series of images of the user during the execution, by the user, of at least one upper-body movement, providing a first trained machine learning model, said first trained machine learning model being trained to associate an intermediate quantified value of an occurrence probability of a stroke condition with features representative of series of images and sounds of the user during the execution of instructions corresponding to:

an execution, by the user, of at least one facial movement, an execution, by the user, of at least one upper-body movement, a pronunciation, by the user, of at least one group of words, providing the extracted features for each instruction to said first trained machine learning model and receiving, by the computing device, the several intermediate quantified values of an occurrence probability of a stroke condition, providing a second trained machine learning model, said second trained machine learning model being trained to classify said several intermediate quantified values using a database containing at least pre-labeled stroke condition data and other data related to a training set of patients;

providing, on a computer interface, the several received intermediate quantified value of an occurrence probability of a stroke condition to said second trained machine learning model, and determining a final quantified value of an occurrence probability of a stroke condition in accordance with said several intermediate quantified values receiving, by the computing device, the final quantified value of an occurrence probability of a stroke condition, and providing, on a computer interface, the final quantified value of an occurrence probability of a stroke condition.

8. One or more non-transitory computer-readable media storing instructions that, when executed by one or more processors, cause a computing device to:

providing, by a computer interface, at least three instructions to a user, at least three said instructions corresponding to:

an execution, by the user, of at least one facial movement, an execution, by the user, of at least one upper-body movement, a pronunciation, by the user, of at least one group of words, capturing, by at least one capturing device, a series of images and sounds of the user during the execution of each instruction, extracting, by a computing device, features from each series captured, in which the step of extracting comprises a step of determining, by the computing device, at least one position of at least one wrist of the user along at least one axis in a series of images of the user during the execution, by the user, of at least one upper-body movement, said at least one position being used as a feature by the trained machine learning model, in which the step determining is configured to determine two series of positions of each wrist of the user along at least one axis in a series of images of the user during the execution, by the user, of at least one upper-body movement, providing a first trained machine learning model, said first trained machine learning model being trained to associate an intermediate quantified value of an occurrence probability of a stroke condition with features representative of series of images and sounds of the user during the execution of instructions corresponding to:

an execution, by the user, of at least one facial movement, an execution, by the user, of at least one upper-body movement, a pronunciation, by the user, of at least one group of words, providing the extracted features for each instruction to said first trained machine learning model and receiving, by the computing device, the several intermediate quantified values of an occurrence probability of a stroke condition, providing a second trained machine learning model, said second trained machine learning model being trained to classify said several intermediate quantified values using a database containing at least pre-labeled stroke condition data and other data related to a training set of patients;

providing, on a computer interface, the several received intermediate quantified value of an occurrence probability of a stroke condition to said second trained machine learning model, and determining a final quantified value of an occurrence probability of a stroke condition in accordance with said several intermediate quantified values receiving, by the computing device, the final quantified value of an occurrence probability of a stroke condition, and providing, on a computer interface, the final quantified value of an occurrence probability of a stroke condition.

*    *    *    *    *